United States Patent
Zdeb et al.

[11] Patent Number: 5,820,605
[45] Date of Patent: Oct. 13, 1998

[54] RETRACTABLE SYRINGE

[76] Inventors: Brian D. Zdeb, 2 E. Lakeshore Dr., Round Lake Park, Ill. 60073; Jerry Goldberg, 2614 Cason, Houston, Tex. 77005

[21] Appl. No.: 395,551

[22] Filed: Feb. 28, 1995

Related U.S. Application Data

[63] Continuation-in-part of Ser. No. 934,521, Oct. 4, 1992, Pat. No. 5,393,301, which is a continuation-in-part of Ser. No. 771,762, Oct. 4, 1991, Pat. No. 5,205,823, which is a continuation-in-part of Ser. No. 592,623, Oct. 4, 1990, Pat. No. 5,112,315.

[51] Int. Cl.$^6$ ..................................................... A61M 5/00
[52] U.S. Cl. ........................................... 604/195; 604/110
[58] Field of Search ..................................... 604/195, 110, 604/192, 198, 187, 263, 218, 220, 228

[56] References Cited

U.S. PATENT DOCUMENTS 5,462,531  10/1995  Novacek et al. ..................... 604/195 X

*Primary Examiner*—John D. Yasko
*Attorney, Agent, or Firm*—David M. Ostfeld

[57] ABSTRACT

A retractable syringe includes a barrel, one end of which comprises a mounting collar. A needle carrier is releasably mounted within the collar and releaseably supports a needle cartridge. A hypodermic needle is mounted within the cartridge. A sheath attaches at one end of the cartridge and at the other end of the collar. A plunger is telescoped into the barrel and includes a piston sealingly engaging the barrel. The piston includes a latch for engaging the carrier and releasing it from the collar. The piston and carrier also include an anti-remount mechanism preventing the carrier from being reengaged into the collar. To preform this, a separate tool is used to insert the carrier into the collar. The plunger further includes surfaces to displace fluid as the piston is forced toward the proximal end of the barrel to displace fluid to reduce squirt. A cap is also provided to initially seal off the proximal end of the barrel and after usage to form a seal by engaging teeth within the proximal end of the barrel.

15 Claims, 12 Drawing Sheets

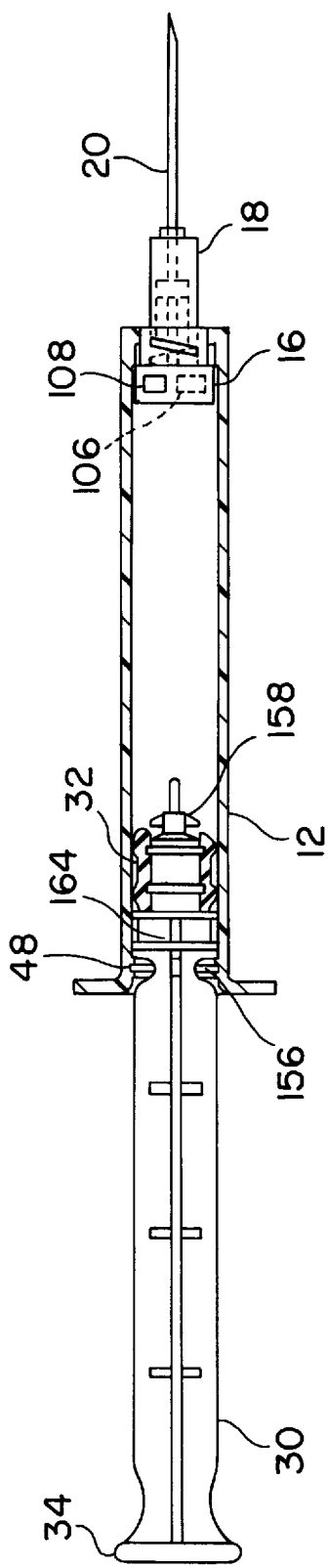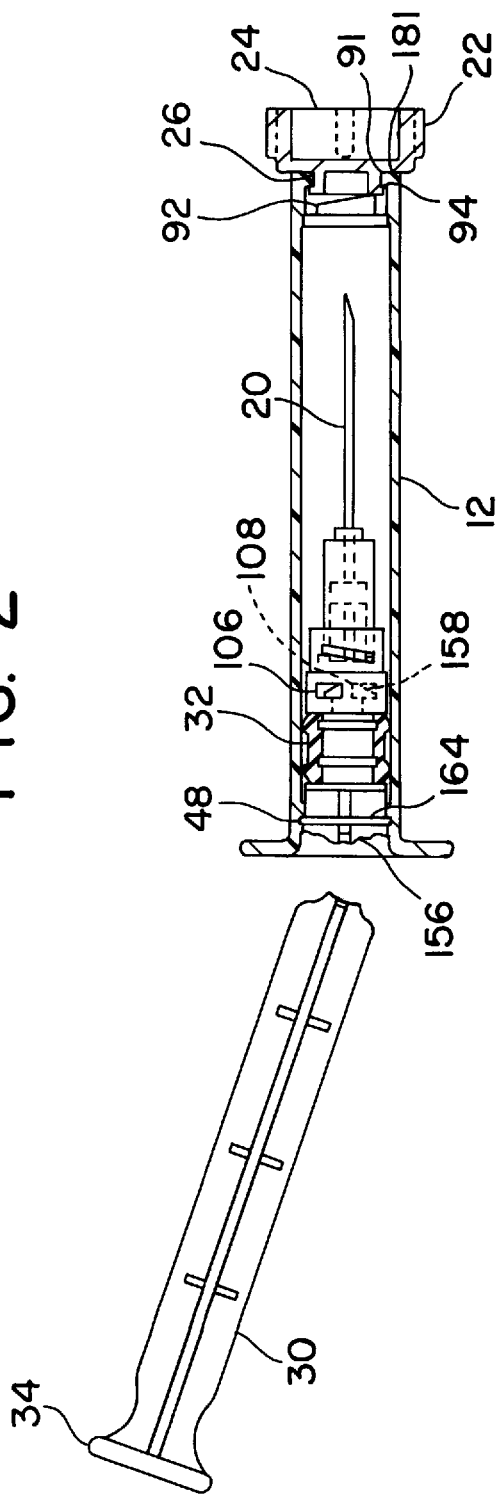
FIG. 2
FIG. 3

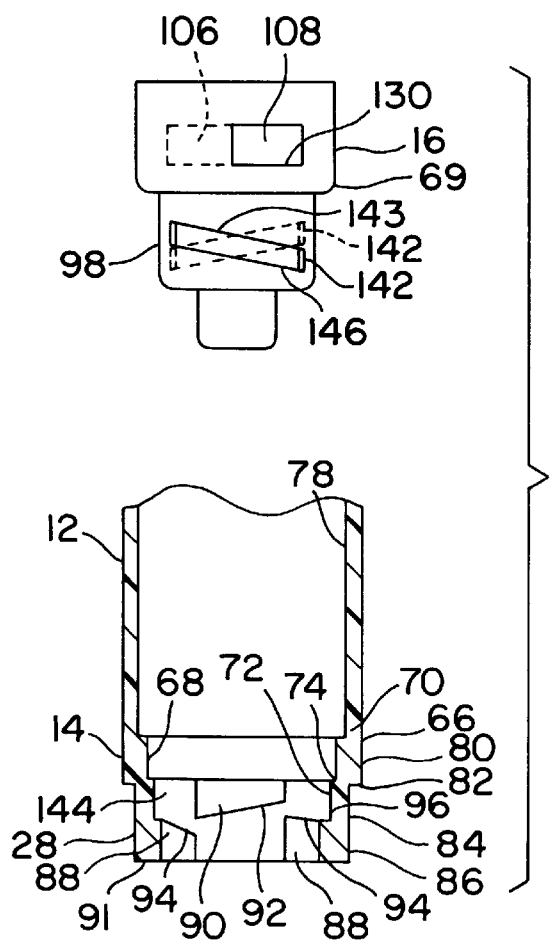
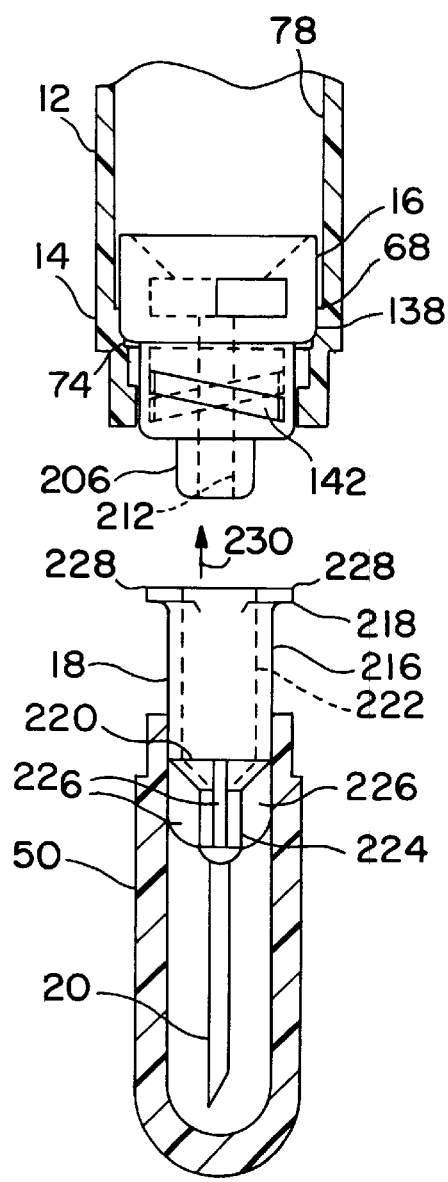
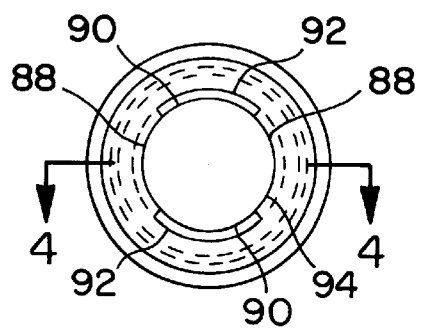
FIG. 4
FIG. 4A
FIG. 5

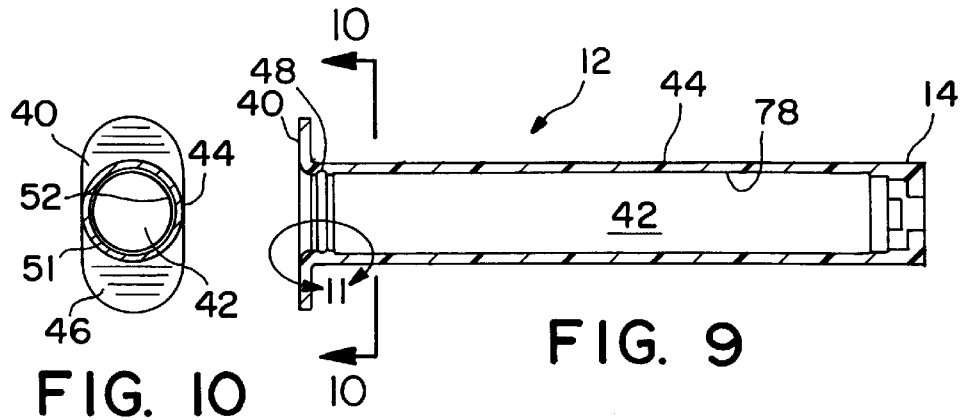
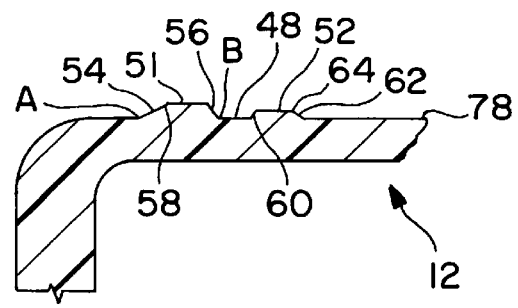
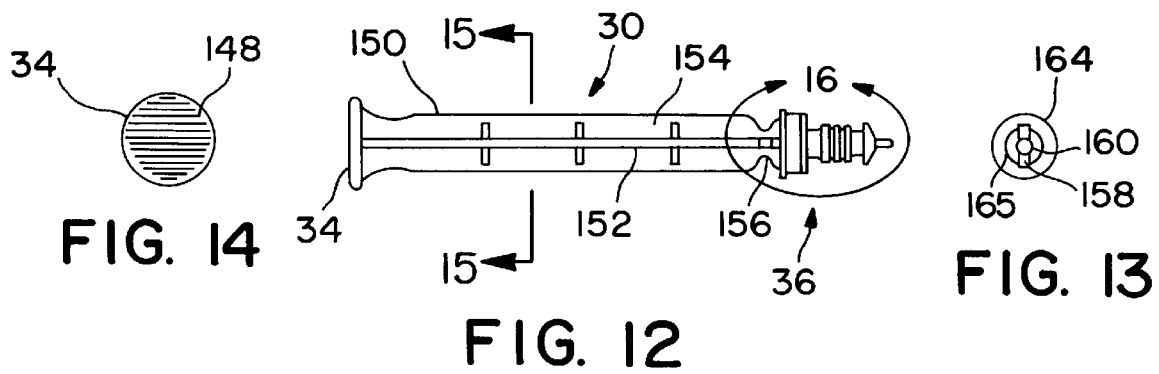

RETRACTABLE SYRINGE

CROSS REFERENCED TO RELATED APPLICATIONS

This application is a continuation-in-part of U.S. application Ser. No. 07/934,521, filed Oct. 4, 1992 now U.S. Pat. No. 5,393,301 for Retractable Syringe by Jerry Goldberg which was a continuation-in-part of U.S. application Ser. No. 771,762, filed Oct. 4, 1991 now U.S. Pat. No. 5,205,823 by Brian Zdeb for Retractable Syringe which is a continuation-in-part of U.S. application Ser. No. 592,623, filed Oct. 4, 1990 now U.S. Pat. No. 5,112,315 by Walter W. Gloyer and Frederick G. Bright for Improvements in Safety Disposable Syringe.

BACKGROUND OF THE INVENTION

1. Field of the Invention

The present invention relates generally to retractable hypodermic syringes, and more particularly to a retractable hypodermic syringe having a needle carrier adapted for releasably attaching a needle cartridge thereto prior to use.

2. Background

In the past, needle stick injuries suffered by medical personnel and others in the course of using hypodermic syringes have presented a serious problem. Serious diseases such as hepatitis and AIDS may be transmitted by needle stick injuries, resulting in the suffering, and possibly even in the death, of the unfortunate victims. Of late, the onslaught of AIDS has resulted in needle stick injuries posing even greater health hazards because of the virtual certainty of death, at least insofar as research to date indicates, of the injured person if he or she contracts the disease.

In order to minimize the risk of needle stick injuries, retractable syringes have been developed which enable the retraction of the needle into the barrel of the syringe following use and prior to disposal. The movement of the needle in the retracted position is typically limited such that normally it will not again protrude from the barrel, and normally will not again come in contact with a health care worker or other person. Retraction and retention of the possibly contaminated needle into the barrel thus protectively isolates the needle and keeps it out of further human contact under normal circumstances. Such a retractable syringe is shown, for example, in U.S. Pat. No. 5,205,823 issued Apr. 27, 1993, to Brian D. Zdeb, also an inventor herein, the disclosure of which is hereby incorporated by reference as if fully recited herein, including the references to the citations of the state of the art.

At times, persons having a need to use a hypodermic syringe in health care operations will commonly select a particular needle bore and length depending on the patient, the medication to be injected, the rate of injection and the injection site. The trend, in most cases, is to use the needle with the smallest acceptable bore and shortest length since smaller bore needles are less painful to the patient and easier to insert into small veins or arteries, if these are the points of injection. It is therefore common for health care workers to select a hypodermic syringe without a needle and then select the required needle for the procedure.

Sterile hypodermic needles are commonly supplied in individual closed sheaths which provide a means to maintain sterility of the needle and facilitate attachment of the needle to the syringe luer connection after the syringe luer cover is removed. Once the syringe luer cover is removed, then the needle luer, with the needle sheath, is placed onto the syringe luer connection, the needle sheath is typically left attached to retain sterility and prevent needle sticks during transport. The syringe cover, which covered the syringe luer outlet prior to attachment of the needle, cannot be reused and, therefor, is usually discarded.

The hypodermic needle with sheath described above is typical in the industry. With conventional non-retractable syringes, the protective sheath may be reinstalled on the needle following use, but such reinstallation also involves the inherent risk of needle stick from the improper or careless handling of the tip of the needle, the sheath, or both. Research studies have proven that needle sheath reinstallation is a major cause of needle sticks. Sometimes the person attempting to reinstall the sheath may not be physically able to do so easily, as might be the case, for example, if the person were to suffer from arthritis, a nerve disorder, or similar problem. Moreover, the U.S. Center for Disease Control guidelines now prohibit the recapping of syringes with the needle covers after use.

Following the use of a retractable syringe, there is no need to reinstall the protective sheath, so the risk of a needle stick arising from reinstallation is eliminated.

There is another potential disease-causing contamination problem, however, in that the syringe barrel is left open following retraction of the needle, or space for fluid is left which must be decreased as part of the needle retraction operation, thereby permitting any excess fluid or residue left in the barrel or the space, respectively, to leak out or be forced out, respectively, into the environment. For example, if the excess fluid or residue were to be a fluid or residue contaminated with bacteria or a virus, there is a risk of this contamination spreading to other medical tools or equipment in the area, possibly infecting persons who subsequently come into contact with such tools, equipment or the syringe. The needle sheaths typically used in the past for covering the needles are incapable of being used to enclose the barrels of retractable syringes following use and retraction of the needle into the barrels, so as to prevent such leakage and environmental contamination.

Yet another potential disease-causing contamination problem with retractable syringes is the possibility of remounting and resealing the needle carrier to the mounting collar, after the needle has been retracted, resulting in exposure of the needle and allowing for reuse of the syringe assembly.

It is an object of the present invention to provide a retractable syringe with a common barrel configuration which will reliably accept a needle luer connection with a needle of virtually any desired commercial size or shape.

It is another object of the present invention to provide a simple means to both seal the outlet end of the syringe barrel before connection of the needle, in order to maintain initial sterility, and after use and retraction of the needle, in order to maintain a positive non-contaminating barrel seal, by special cap seals which seal the outlet end of such syringe both before and after use.

It is another object of this invention to provide a means to allow easy assembly of the needle carrier to the barrel mounting collar during manufacture by special manufacturing assembly tools for assembly of a needle carrier to the mounting collar of the hypodermic syringe while at the same time preventing re-assembly and sealing of the needle carrier to the mounting collar after release of the needle carrier from the mounting collar either before or after retraction of the needle into the syringe barrel.

It is another object of the present invention to reduce fluid from squirting from the needle, when making-up the needle retraction assembly, by reducing the internal residual volumes of entrained fluids which may be discharged from the needle during the needle retraction make-up process.

It is another object of the present invention to provide such a syringe which is durable, reliable, easy to use, inexpensive, and simple to manufacture.

SUMMARY OF THE INVENTION

According to the preferred embodiment of the invention, a retractable syringe includes a barrel, one end of which comprises a needle carrier mounting collar. A needle carrier is releasably mounted, only during manufacture through the distal end, within the mounting collar, and is adapted to releasable support a needle with included luer connection. An invertible safety cover is adapted to be frictionally retained to the hub of the mounting collar of the barrel to provide a sterile cover prior to needle connection and, in the inverted position, to seal the retracted needle into the barrel. Alternately, a separate cover can be used for sealing the barrel after needle retraction.

The needle carrier is sealingly mounted through the distal end of the barrel within the mounting collar with a special mounting tool during manufacture. The mounting tool has geometry which matches only specific geometry within the inner pocket of the needle carrier. The needle carrier is mounted to the mounting tool by placement of the matching needle carrier recess over the mounting tool and insertion of the needle carrier into the distal end of the barrel. Upon insertion of the needle carrier into the mounting collar, the mounting tool is twisted to force the needle carrier into engagement with matching, external, partial bayonet style threads of the needle carrier and the internal, bayonet style mounting threads of the mounting collar. The twisting motion results in forcing the matching bayonet threads into sliding engagement resulting in a sealing interference engagement of the circumference of the needle carrier with a diameter of the mounting collar. The mounting tool is then withdrawn.

The needle carrier includes an axial bore extending through the luer connection and in fluid communication with the inside of the barrel. The needle carrier luer end includes a blind circular pocket surrounding the luer connection. This blind circular pocket contains internal threads, commonly called luer lock threads, to provide engagement and locking means for the tabs common to industry standard needle hub luer connections or, alternately, special tabs for a non-standard needle hub if specified.

An elongate plunger is telescoped into and carried within the barrel. The plunger includes an injection piston attached at its proximal end, disposed within and sealingly engaging the barrel. The proximal face of the piston includes a stinger 158 latch at or near its center.

The stinger latch is adapted to engage, in one direction only, a seat in the recess of the needle carrier in such a fashion that rotation of the stinger latch in one direction also rotates the needle carrier in the same direction, ultimately resulting in unsealing the end of the barrel of the needle carrier from the mounting collar seat without excessive fluid discharge. Once the needle carrier seal is dislodged from the mounting collar, a ramp opposite the carrier recess prevents rotation in the opposite direction by reducing friction and causing the stinger latch to slide up along the ramp surface and out of the needle carrier recess thus preventing resealing and reuse of the syringe assembly.

Once the needle carrier is dislodged from its seat and fully rotated to its maximum position, then the piston is permitted to withdraw back into the barrel with the needle carrier and attached needle. The invertible cap, or another separate cap, is then threaded into the top bayonet style threads of the mounting collar to seal the barrel end thereby preventing leakage and exposure of the contaminated fluids and needle.

An end of the inside of the barrel is provided with a latching means for latching the plunger in retracted position and securing the needle safely within the barrel. In the preferred embodiment, the latch includes two circumferential rings in close proximity to each other and with a diameter smaller than the barrel bore but not so small so as to interfere with manufacturing assembly and the operation of the piston. The inner most ring is of a diameter slightly larger than the outer ring in order to provide a smooth snap fit with the inner ring while providing a positive stop thus preventing easy or accidental withdrawal of the plunger, needle carrier and attached needle. The protruding portion of the plunger may be broken off substantially flush with the end of the barrel as a result of a reduced diameter, or other such means, of the plunger at the point of protrusion of the plunger from the barrel. The used syringe may then be safely discarded without further danger of a needle stick injury.

These and other objects and advantages of the invention will become apparent from the following description of the preferred embodiments when read in conjunction with reference to the following drawings.

BRIEF DESCRIPTION OF THE DRAWINGS

For a further understanding at the nature and objects of the present invention, in conjunction to this specification, reference should be had to the following drawings in which like parts are given like reference numerals and wherein:

FIG. 2 is a view partly in longitudinal section, partly in phantom line and partly in elevation, taken along section lines 2—2 of FIG. 1, of the retractable syringe of FIG. 1, showing the needle attached to the needle carrier and ready for use.

FIG. 3 is a view partly in longitudinal section and partly in elevation of the retractable syringe of FIG. 1, showing a portion of the plunger, engaged to the needle carrier, withdrawn into the syringe barrel, and a portion of the plunger broken away from the piston. The invertible cap is shown inverted and installed into the mounting collar.

FIG. 4 is a vertical, sectional view of the mounting collar taken along section lines 4—4 of FIG. 4A and a side view of the needle carrier of the embodiment of FIG. 1 in exploded relation with the needle carrier in position prior to being inserted into the mounting collar.

FIG. 4A is a proximal view of the barrel of FIG. 4 and FIG. 9.

FIG. 5 is a vertical view, partly in section and partly in elevation, of the assembled mounting collar, needle carrier and needle of the embodiment of FIG. 1, the needle covered by a cap shown in section.

FIG. 9 is a longitudinal, cross-sectional view of the barrel of the retractable syringe of FIG. 1 and FIG. 8.

FIG. 10 is a proximal end view of the finger flanges of the barrel of FIG. 9 taken across section lines 10—10 of FIG. 9.

FIG. 11 is a detail view of the latching means at the distal end of the barrel of FIG. 9.

FIG. 12 is a side view of the preferred embodiment of the plunger of the retractable syringe of FIG. 8.

FIG. 13 is a proximal end view of the plunger of FIG. 12.

FIG. 14 is a distal end view of the plunger of FIG. 12.

DETAILED DESCRIPTION OF THE PREFERRED EMBODIMENT

Figure 1:
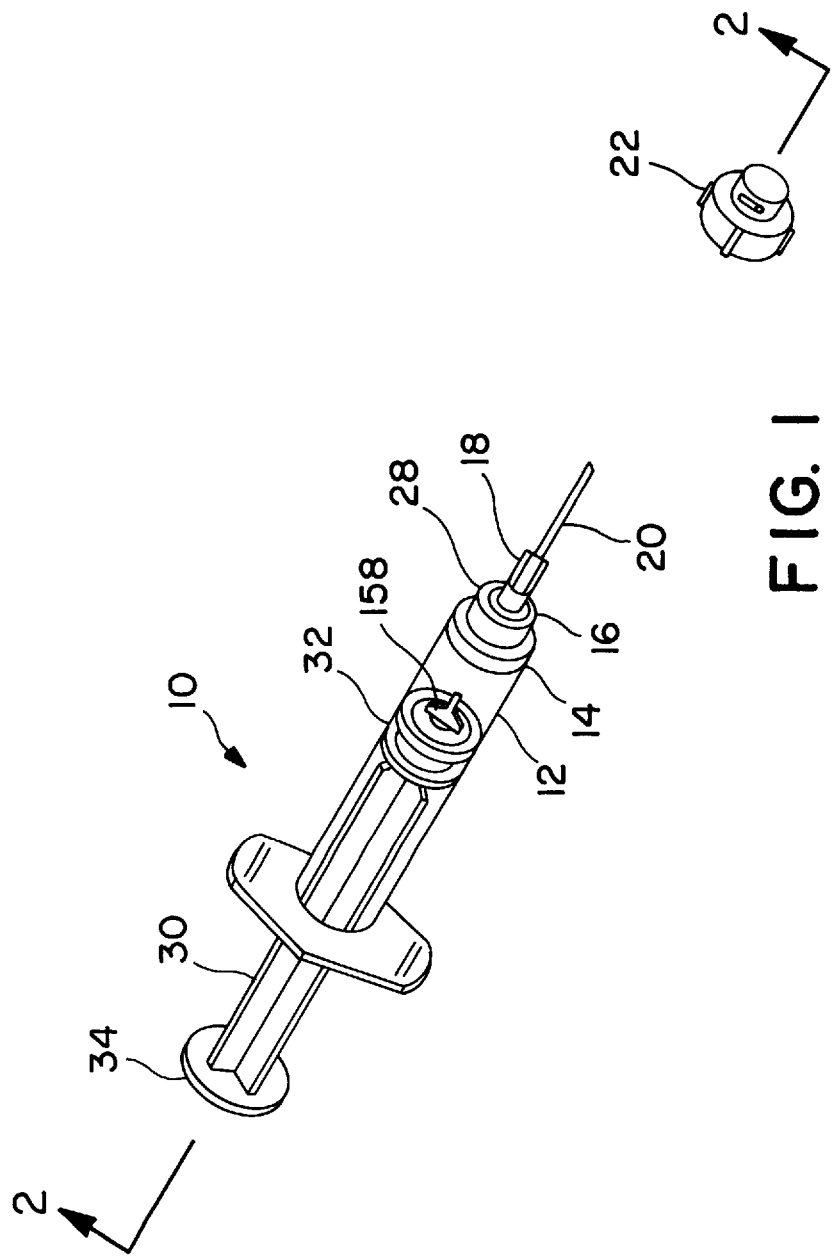
FIG. 1 is an isometric view of the preferred embodiment of a retractable syringe according to the present invention, the syringe being shown in assembled condition with invertible syringe cap and ready for use with connection of the needle.
Figure 6A:
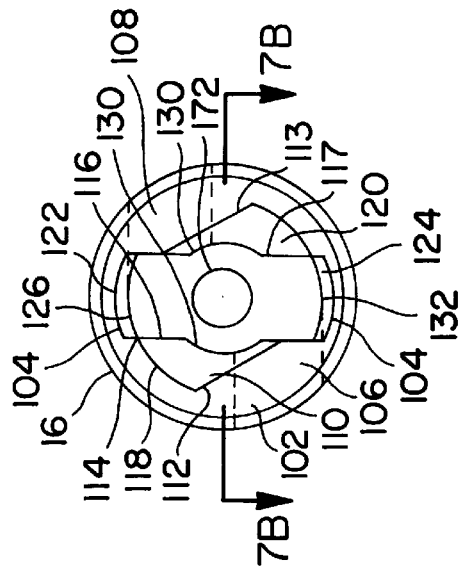
FIG. 6A is a distal end view toward the proximal end of the needle carrier of the embodiment of FIG. 1 and FIG. 8.
Figure 7B:
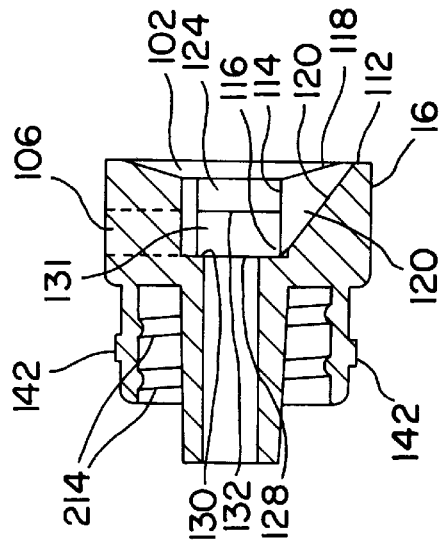
FIG. 7B is a horizontal cross sectional view of the needle carrier shown in FIG. 6A, taken along section lines 7B—7B of FIG. 6A.
Figure 6:
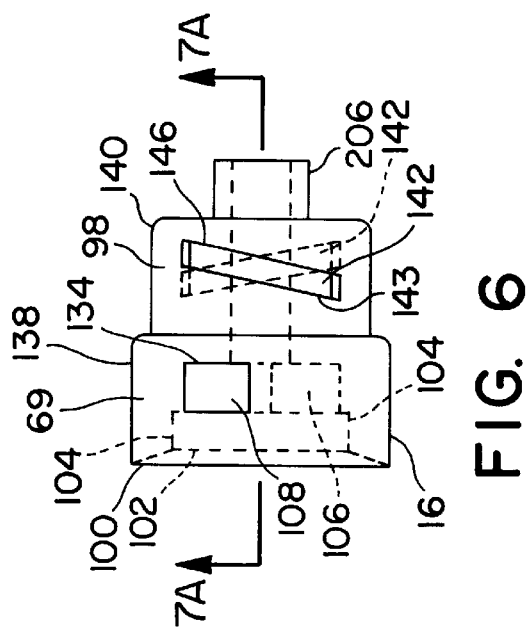
FIG. 6 is a horizontal side view, partly in phantom line, of the needle carrier of the embodiment shown in FIG. 1 and FIG. 8.
Figure 7A:
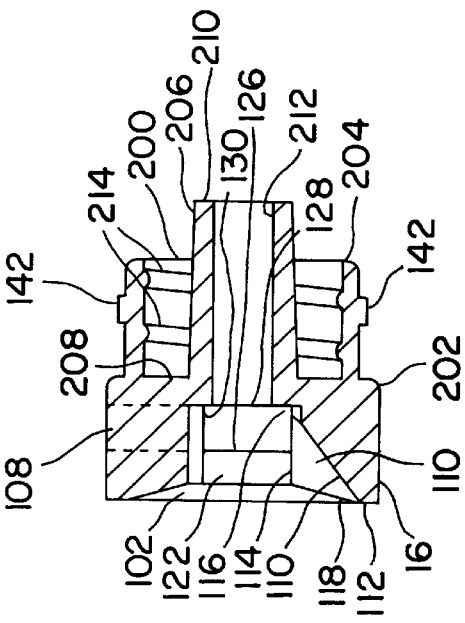
FIG. 7A is a horizontal cross sectional view of the needle carrier shown in FIG. 6, taken along section lines 7A—7A of FIG. 6.
Figure 8:
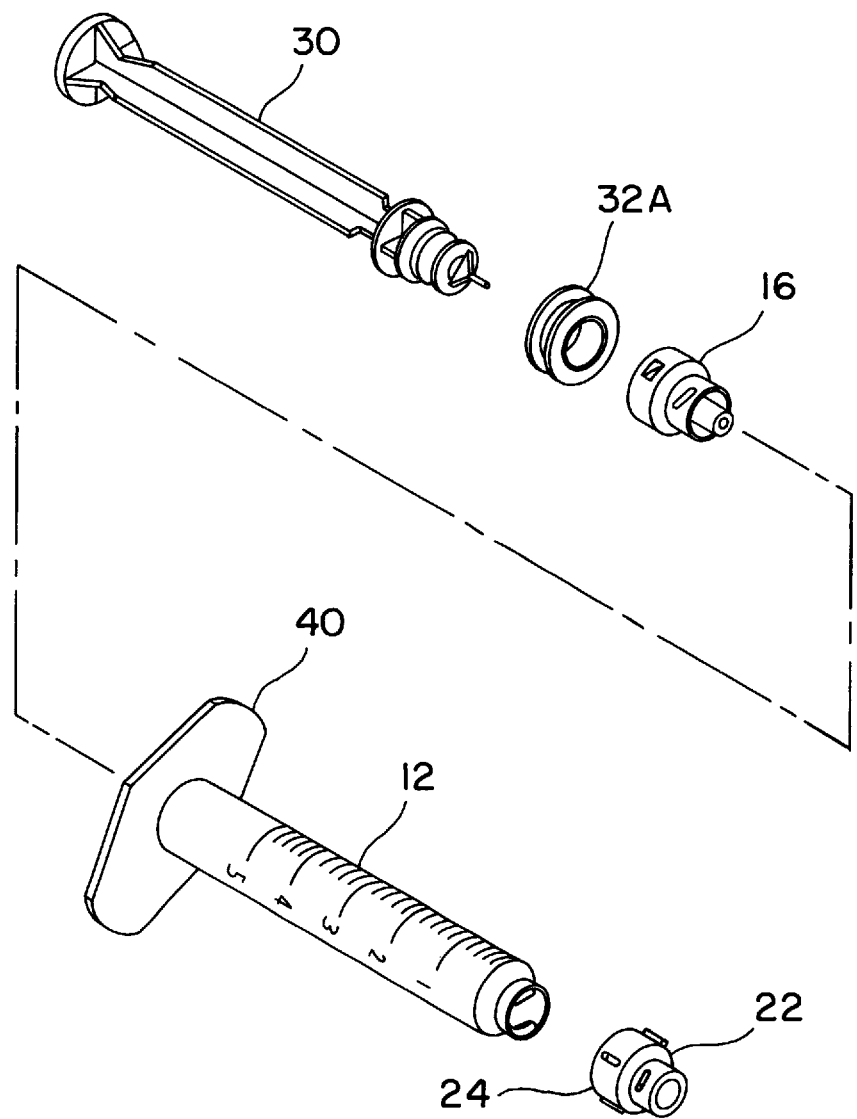
FIG. 8 is an isometric view of the preferred embodiment of a retractable syringe according to the present invention shown in FIG. 1, the syringe being shown in exploded view and without the needle as in FIG. 1 and FIG. 2.
Figure 15:
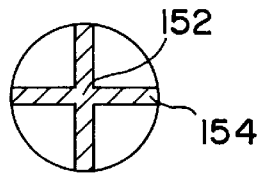
FIG. 15 is a cross sectional view of plunger of FIG. 12 taken along section lines 15—15 of FIG. 12.

Referring first to FIGS. 1 and 8, an isometric view and an exploded view, respectively, are seen wherein a retractable syringe of the present invention is shown in accordance with the principles of the present invention which is designated generally by reference number 10. The device 10 includes a barrel 12, which may be resilient, having at the proximal end, that is, the end nearer the point of a needle, a needle carrier support or mounting collar 14 holding a needle carrier 16 on which is mounted a needle 20. The needle carrier 16, more particularly described below and better shown in FIGS. 4–7, is mounted within the mounting collar 14. Needle carrier 16 is adapted to support therewithin a needle cartridge or female luer 18 on which is mounted the hypodermic needle 20. A needle sheath 50, generally shown in FIG. 5, is frictionally retained on female luer 18 and covers the needle 20 during assembly and prior to use of device 10.

Mounting collar 14 includes a hub 28 formed at its proximal end. An invertible locking safety cover or cap 22 is shown in FIG. 1 having an end 24 (FIG. 3) which prior to frictional removal of end 24 was frictionally held on the hub 28 of mounting collar 14 covering the proximal end of mounting collar 14 prior to use of device 10 and assembly of female luer 18 to needle carrier 16. Invertible cap 22 further includes an end 26 adapted to positively lock to surfaces 94 and sealingly engage the surface wall 181 with the surface of the hub 28 of mounting collar 14 (FIG. 3) to later provide a seal means upon retraction of the needle 20 into the interior of barrel 12, as more particularly described below.

An elongate plunger member 30 is telescoped into the distal end, that is, the end of barrel 12 farthest from the needle 20, and carried within the barrel 12. Plunger member 30 includes a body portion comprising a plurality of longitudinal ribs 32, a thumb rest 34 formed at its distal end and an injection piston 36 attached at its proximal end disposed within barrel 12 and in sealing and sliding engagement within the interior 78 of barrel 12. The proximal face of piston 36 includes a longitudinally extending stinger 158 at or near its center as discussed below.

Plunger 30 including piston 36 may be made of a relatively hard material such as, for example, high density polypropylene or other suitable synthetic material. The outer circumferential periphery of piston 36 is substantially smooth and rounded to provide sealing and sliding engagement against the interior wall 78 of barrel 12. Barrel 12 may be made of a hard or relatively resilient material, including polyethylene or polypropylene, for example. The same material used for barrel 12 may also be employed for protective cover Piston 36 is sized and shaped to serve as a liquid or fluid displacement means within barrel 12 for withdrawing a liquid or fluid substance from another container, for example, and subsequently injecting the substance through needle 20 into a subject being treated. Of course, syringe 10 may be used for withdrawing liquid or fluid substances from a subject for subsequent testing, or for other purposes. In short, the retractable syringe 10 of the present invention may be used in any clinical setting, under any medical conditions.

Barrel 12, having interior 78, as discussed above, includes at its extreme distal end a flange 40. See FIGS. 9 and 10. Flange 40 includes barrel opening 42 having at its exterior the walls 44 of barrel 12. Flange 40 further includes grooves 46, preferably equally spaced and parallel on the surface of its distal end, preferably molded thereon. As best seen in FIG. 11 and FIG. 10, immediately proximal to flange 40, there is formed a groove 48 in the interior wall 78 of barrel 12. Groove 48 is of the same diameter as interior wall 78 and is really a continuation of interior wall 78. Groove 48 is formed by being bounded on its sides by annular constrictions, constriction 51 at the distal end of groove 48 and constriction 52 at the proximal end of groove 48. Both constrictions 51, 52 are of smaller diameter than the interior diameter of wall 78 and groove 48. Distal constriction 51 is of smaller interior diameter than proximal constriction 52. Preferably constrictions 51, 52 have a shape as shown in FIG. 11 which is a truncated triangular shape, forming a trapezoid in cross-section with a base line extension of interior wall 78. The shape can be of any shape that permits passage of plunger 30 into barrel 12, so long as said shape is moldable. Distal constriction 51 includes sides, distal side 54 and proximal side 56. The angle formed between wall 78 and distal side wall 54, angle A in FIG. 11, is generally greater than the angle formed between groove 48 and proximal side 56, angle B in FIG. 11. Thus, on insertion, distal side 54 will be more permissive of insertion of plunger 30 and needle carrier 16, whereas proximal side 56 will be more resistant to retraction. Thus proximal side 56 forms a stop with groove 48 upon the attempted retraction of plunger member 30 from the interior 42 of barrel 12. Distal constrictions 51, 52 are subject to shear during molding if it is too small in length. Thus, the length of interior cylindrical portion 58 is approximately twice or greater than twice the difference in radius of interior wall 78 less the radius of distal constriction 51. Proximal constriction 52 has distal side 60 and proximal side 62. The angle between interior wall 78 and proximal side 62, is approximately angle A. The angle between distal side 60 and interior wall 78 is approximately angle B. The depth, the difference between the radius of interior wall 78 and the radius of flat portion 64 of proximal constriction 52 is approximately one-half of the depth of distal constriction 51. Thus, proximal constriction 52 acts as a snap fit to hold plunger member 30 in groove 48 after retraction, as discussed in the following. The form of the distal constriction 51 and proximal constriction 52 is different from that of other Background materials in order to achieve easy insertion and to avoid shearing these constrictions during molding. By having the snap fit, there is resistance during the process of breaking off the plunger 30 that reduces the potential for the plunger 30 to move forward while it is being handled. If the plunger 30 does move forward it could inadvertently cause a stick. Other materials in the Background do not show or include a snap fit except Zdeb, and with only a stop there would be easy forward motion of the piston during piston break that could cause inadvertent stick. Also, without the snap fit, the needle and plunger assembly would be free to slide forward, exposing the needle, if the invertible cap is not in place. With the snap fit, for assembly, force must be applied to cause the plunger 30 to move over proximal side 56.

The proximal end of barrel 12 is shown in FIGS. 4, 4A and 5. The barrel 12 has as its proximal end carrier mounting collar 14. The mounting collar 14 includes a first hub portion or first constriction or relatively thick-walled section 66 having a tapered interior wall 68 having a frusto-conical shape. The angle between extension of the base cylinder of interior wall 78 and the wall 68 would range between zero degrees and three degrees and preferably at one and one-half degrees. Thus, wall 68 would form a negative draft with wall 78 of zero to three degrees for a total included angle maximum of six degrees, and preferably three degrees. Thus, the diameter of the proximal end of wall 68 is smaller than the diameter at the distal end of wall 68. This angle is formed to create a point contact for interference with the needle carrier 16 as discussed below to seal or enhance the sealing of the needle carrier 16 to wall 68 through an interference fit with a flange 69 of needle carrier 16. Flange 69 of needle carrier 16 is received in the interior of wall 68 through the distal end of wall 68 when the needle carrier 16 is locked in place in mounting collar 14. Flange 69 is preferably somewhat resilient, so that it will sealingly engage wall 68 when carrier 16 is locked into place in collar 14.

As shown in FIG. 4, wall 68 and wall 78 form an annular shoulder 70 therebetween. For smaller diameter interior walls 78, said shoulder 70 does not need to exist. However, as the diameter of wall 78 increases, it is necessary to have a shoulder 70 in order to define the position of the needle carrier 16 when it begins an interference fit. This is preferable in the design in order to be able to set the dimensions of needle carrier 16 as discussed below. Thus, wall 68 always has a fixed length, preferably starting with distal shoulder 70.

At the proximal end of wall 68, there is formed a cylindrical wall 72, forming a proximal shoulder 74 between wall 72 and wall 68. Shoulder 74 may not be present depending on the dimensionality of wall 68 and wall 72, but when it is present, it acts as an outer stop for the insertion of needle carrier 16 into carrier mounting collar 14 should the thread discussed below be improperly set. In fact, in FIG. 5, the shoulder 74 is not used as a stop because the thread is properly set as discussed below.

As shown in FIG. 4, the exterior wall 80 of the constriction section 66 of mounting collar 14 forms a shoulder 82 with the distal end of exterior wall 84 of stepped proximal portion 86 of mounting collar 14. Shoulder 82 is formed for large diameter barrels 12. However, as shown in FIG. 2, where the barrel 12 is of a smaller size, shoulder 82 would not be necessary. Shoulder 82 becomes necessary in order to have a stepped proximal portion 86 for the larger diameters of barrel 12 in order to standardize on the size of needle carrier 16.

Cylinder wall 72 at the proximal end of mounting collar 14 contains four internal quarter threads, two internal, diametrically opposed, substantially longitudinal extending quarter threads 88 which are proximal quarter threads and two other internal, diametrically opposed, substantially longitudinally extending quarter threads 90 which are distal of quarter threads 88, the two such threads 90 extending in a proximal direction from the interface between wall 68 and wall 72, and the two such threads 88 extending in a distal direction from the proximal end 91 of barrel 12.

All threads are formed in the molding process, preferably. The quarter threads are used rather than a continuous thread in order to facilitate the molding process and to keep expenses lower as a result of such facilitation. By using quarter threads there is only the necessity in the molding process of pushing together and pulling apart the mold rather than having to have a screw mechanism rotating with regard to the mold.

Threads 90 have a cross-sectional profile of a trapezoid, preferably. As shown in FIG. 4, the proximal surface 92 of lower internal quarter threads 90 is slanted in cross-section yielding a left hand thread. Preferably the angle of proximal surface 92 is ten degrees with a plane orthogonal to the longitudinal axis of barrel 12. Commonly this thread would be called a ten pitch thread. The left hand thread is used so that when retraction occurs, as discussed below, elongate plunger 30 will be rotated to the right for retraction, which is preferable for the operator of the device. With the spacing of quarter threads 90, mounting collar 14 includes a pair of diametrically opposed, substantially longitudinal extending slots 144 formed in the wall 72 and adjacent quarter threads 90. Thus, the slots 144 intersect with the base of and communicate with the upper surface 92 of the incline threads 90 that are in the wall 72 and, as discussed above, extend part way, for example, ninety degrees or less, around the inside wall 72. The distal surface 94 of upper internal quarter thread 88 is also slanted and upper internal quarter thread 88 is also trapezoidal in cross-sectional shape, surfaces 94 being substantially an end of slots 144. Because of the inclined nature of quarter threads 88, rotation of the needle carrier 16 to the left (quarter threads 90 being left handed as discussed above) will tend to draw the needle carrier 16 more tightly into the mounting collars 14 and will tend to further energize the seal between flange 69 and wall 68. Distal surface 94 forms a ten degree pitch, as does proximal surface 92, the orthogonal plane crossing at point 96 as seen in FIG. 4. Because of the phantom line, FIG. 4A shows the distal facing surface 94. Distal surface 94 is right hand threaded and is thus slanted opposite to proximal facing surface 92. As noted elsewhere, surfaces 94 assist in forcing the carrier back during retraction. If threads 94 were not present, then the carrier would only rotate in the mounting collar. The threads could be separated by less than 90°. Distal surface 94 is right hand threaded in order to facilitate the use of the cap 22 to seal after the needle has been retracted as discussed below. In essence the cap 22 then would be turned in a right circular manner as a right hand thread. Thus, upper internal quarter threads 88 and lower internal quarter threads 90 are substantially identical to those shown in the Zdeb patent discussed above. This is generally true of mounting collar 14. The barrel 12 terminates at proximal surface 91.

Referring now to FIGS. 2, 4 and 5, needle carrier 16 is mounted within mounting collar 14 of barrel 12 from outside barrel 12, as discussed subsequently. Further, needle cartridge 18 is subsequently mounted to the proximal end of needle carrier 16 from outside barrel 12. FIGS. 4, 5, 6, 6A, 7A and 7B depict needle carrier 16. The exterior of needle carrier 16 is comprised of two co-axial cylinders, distal cylinder 69 and proximal cylinder 98, each having a slight rounding at its proximal end. The distal end 100 (FIG. 6) of distal cylinder 69 includes a frusto-conical opening 102. The proximal end of frusto-conical opening 102 terminates with coaxial cylindrical surface 104. A portion of surface or key way 104 includes the sides 122, 124 of the key way which has bottoms 126, 132. Ramps 110, 120 are bounded perpendicular to intersection or bottom 116, 117 by ramp boundary line 114. Surface 104 terminates at key way bottom first side 126 and key way bottom second side 132 of a key way 104. Ramps 110, 120 angle outward in the proximal direction from surface 102 at line 112, 112A at a preferred angle of thirty-five to forty-five degrees, preferably forty degrees, terminating at intersection 116. Key way 104 creates an opening larger than arcuate surface 118 for use with key way assembly tool 136 to be described below. Ramp intersections or bottom edges 116 and 117 terminate at bottom 130 of stinger pocket 131. At the proximal end or bottom 130 of the stinger pocket 131, for which bottom 130 is the most proximal end, extends luer opening 128 which extends through the needle carrier 16 to eventually be in fluid communication with female luer 18. Thus, the opening formed by concentric openings 128, 131, 124, 122, 102 provides fluid communication from the interior of barrel 12 to female luer 18.

Pockets 106, 108 are formed in mounting collar 16 for manufacturing purposes. Pockets 106, 108 are orthogonal to the axis of needle carrier 16. Pockets 106, 108 are further required for the proper molding of needle carrier 16. By receiving metal inserts (not shown) that are part of the molding process space is reserved in the interior of needle carrier 16 which formed the pockets 106, 108 which are interlocks to the stinger described below.

The proximal end 134 of pockets 106, 108 is located on the distal side of a seal surface 138 along the surface of distal cylinder 69, wherein the surface of distal cylinder 69 seals against the interior surface 68 of mounting collar 14 (as best seen in FIG. 5). As discussed above, the seal 138 is formed by an interference fit between the sealing surface 138 and the inner surface 68 of collar 14. This is caused by the insertion of the carrier 16 into mounting collar 14 as discussed above and below. Thus, the fact that pockets 106, 108 are in fluid communication with luer opening 128 is not material because the pockets 106, 108 are on the distal side of sealing surface 138. Therefore, they cannot cause a leak around sealing surface 138.

The exterior surface 140 of proximal cylinder 98 includes two threads 142 spaced apart one hundred and eighty degrees which match with the proximal surfaces 92 of lower internal quarter threads 90. Thus, when carrier 16 is inserted into collar 14 as shown in FIG. 5, this latches the carrier 16 in the collar 14 and forms the seal surface interference fit with seal surface 138 and surface 68. Threads 142 are inserted into the spaces 144 between lower internal quarter threads 90, and distal surfaces 94 act as stops to indicate to the operator the bottoming out of the threads 142 for make-up against proximal surfaces 92. When the threads 142 are to be unmade so that their distal surfaces 143 are no longer in contact with proximal surfaces 92, distal surfaces 94 act against proximal surfaces 146 of threads 142 to force the dismount of carrier 16 from mounting collar 14 by causing surface 143 to slip past surface 92. If surfaces 94 were not present, there would be rotation without dismount because the interference fit would still be maintained, and there would be a necessity to apply axial force in a distal direction to dismount the carrier 16 from collar 14. Lubricant not shown may be included on surface 68 of carrier 16 to enhance assembly and sealing of carrier 16 in mounting collar 14.

As discussed in the Zdeb patent, a substantially annular blind bore 200, comprising a needle cartridge receiving pocket, extends longitudinally part way, preferably about half way, through the main body 202 from its proximal end 204. In the center of blind bore or pocket 200, there is disposed a needle cartridge support member 206, which may be integral, for example, with main body 202. Needle cartridge support member 206 extends from the distal end wall 208 of pocket 200 beyond the plane of the proximal end face 204 of main body 202, such that a substantial proximal end portion of member 206 protrudes out of the main body 202. Needle cartridge support member 206 is substantially circular conical in configuration and tapers slightly from its distal end at end wall 208 to its proximal end 210. Needle cartridge support member 206 has a longitudinally extending central axis bore 212 therein, in fluid communication with luer opening 128. Pocket 200 has a pair of relatively steeply pitched, raised, that is, radially inward projecting, axial spaced apart helical ribs 214 around its outer wall, forming a pair of lands upon which a corresponding pair of tabs 228 disposed on the distal end of needle cartridge 18 ride in removing or installing the needle cartridge 18, as more fully set out below. The ribs 214 begin, or intersect, the proximal end face of main body 202, on diametrically opposed sides thereof.

Referring now particularly to FIG. 5, the needle cartridge 18 of the present invention is shown in more detail. Needle cartridge 18 shows a elongate generally conical, hollow main body 216 which tapers slightly from its upper or distal end 218 to its lower or proximal end 220. Main body 216 of needle cartridge 18 has a tapered, longitudinally extending, central axis bore 222 which has a taper substantially the same as the taper of the outside surface of needle cartridge support member 206, so as to form a close fit therewith when installed on syringe 10. Bore 222 is in fluid communication with bore 212 in needle cartridge support member 206. Needle cartridge 18 also includes a substantially circular cylindrical extension portion 224 extending in a proximal direction from proximal end 220 of main body 216. A plurality of substantially longitudinal extending stiffening ribs 226 are disposed on main body 216 and extension portion 224 along their outer sides, there being preferably four such ribs 226 at substantially 90° to one another. Cylindrical extension 224 of needle cartridge 18 has a central axial bore therethrough, which is in fluid communication with bore 222 of main body 216. A hypodermic needle 20 of selected size and shape is mounted within the central axial bore in cylindrical extension 224. Needle 20 has a longitudinally extending bore therethrough of selected diameter which bore includes communication with the bore of cylindrical extension 224 and bore 222 and, hence, bore 212 of needle cartridge support member 206.

The upper or distal end 218 of needle cartridge 18 includes a pair of diametrically opposed, outwardly extending tabs or ears 228. When the distal end 218 of needle cartridge 18 is inserted longitudinally axially into needle carrier 16 from the proximal end thereof, as shown by direction arrow 230 and rotated to the right (for a right-handled thread 214; to the left for a left-hand thread), each of the tabs 228 engages and travels along one of the helical threads 214 which draws needle cartridge 18 onto needle cartridge support member 206 and forces needle cartridge 18 into secure, stable, sealed relationship with the needle cartridge support member 206. The tight frictional engagement of tabs 228 into the walls of pocket 200 provides additional lateral stability and support of needle cartridge 18 when mounted in needle carrier 16.

As shown in FIGS. 8 and 12 through 19, plunger 30 and injection piston 32A or alternate injection piston 32 are shown in a state where they are not made up as they are in FIG. 1.

The distal end of plunger 30 includes the extreme distal end 34 which has grooves 148, preferably parallel, formed thereon preferably by the molding process. Distal end 34 swages into the main body 150 of plunger 30. Main body 150 has a central axial portion 152 from which extend vanes 154 (FIG. 15) which are orthogonal to each other. The proximal end of vanes 154 have a detent 156 formed therein in order to weaken the vanes 154 at this point. The vanes 154 render plunger 30 frangible permitting a break along any of the detents 156 to cause the main shaft of the plunger 30 to separate from its proximal end as a result of shear force (FIG. 3). It should be noted that other shapes would be just as suitable for plunger 30 as long as they formed a portion which is frangible upon the application of shear force.

Figure 16:
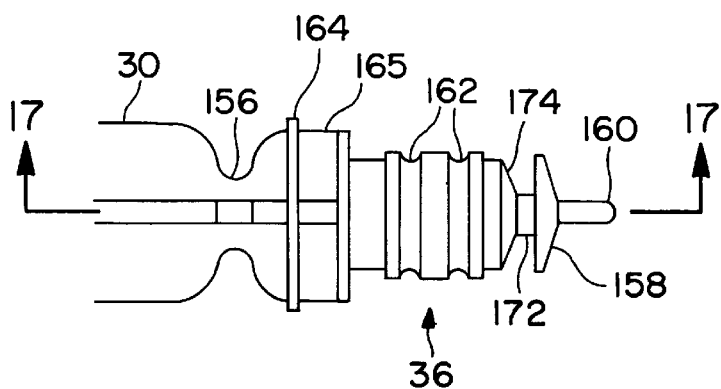
FIG. 16 is a detail view of the proximal end of the plunger of FIG. 12.
Figure 17:
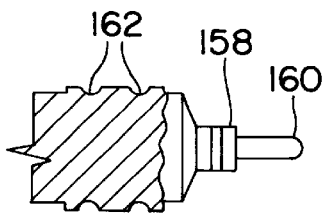
FIG. 17 is a partial cross-sectional view of the proximal end of the plunger of FIG. 12 taken along section line 17—17 of FIG. 16.
Figure 18:
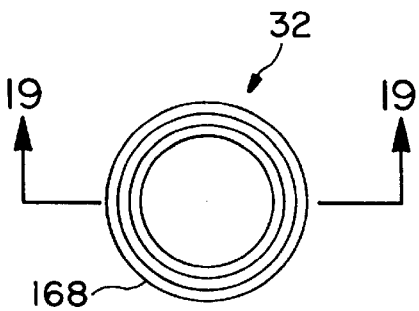
FIG. 18 is an end view of the preferred embodiment of the piston of FIG. 8.
Figure 19:
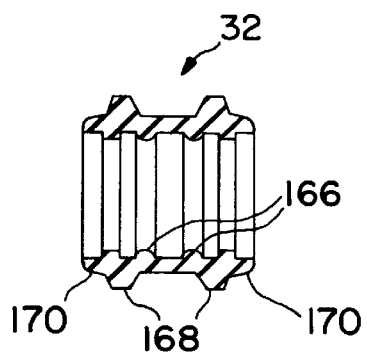
FIG. 19 is a longitudinal, cross-sectional view of an alternate embodiment of the piston of FIG. 18 taken along section lines 19—19 of FIG. 18.
Figure 19A:
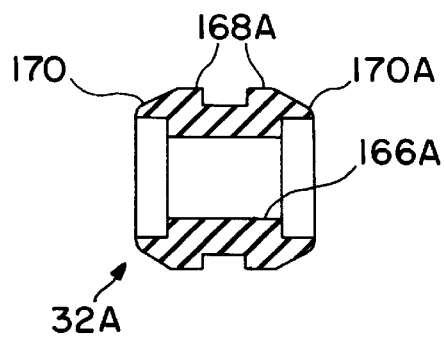
FIG. 19A is a longitudinal, cross-sectional view of the preferred embodiment of the piston.
Figure 19B:
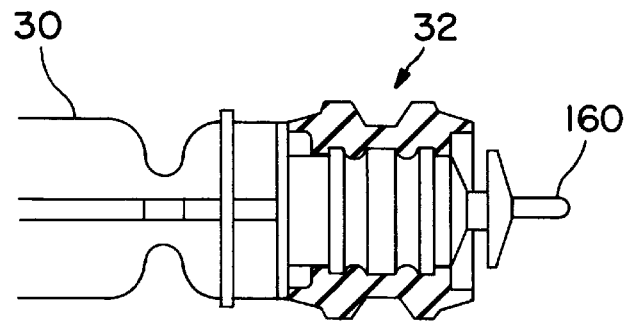
FIG. 19B is a cross-sectional view of the piston assembly to the plunger for the alternate embodiment.
Figure 19C:
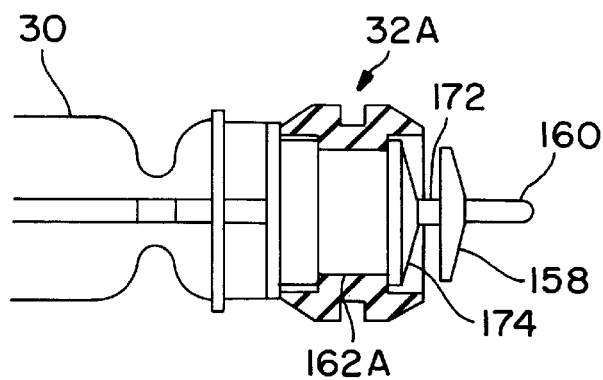
FIG. 19C is a cross-sectional view of the piston assembly to the plunger for the preferred embodiment.
Figure 20:
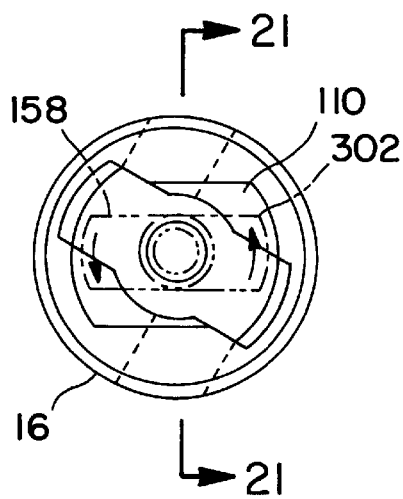
FIG. 20 is a distal end view of the preferred embodiment of needle carrier which includes the plunger stinger shown during reverse or releasing counterclockwise rotation of the stinger from the carrier.
Figure 21:
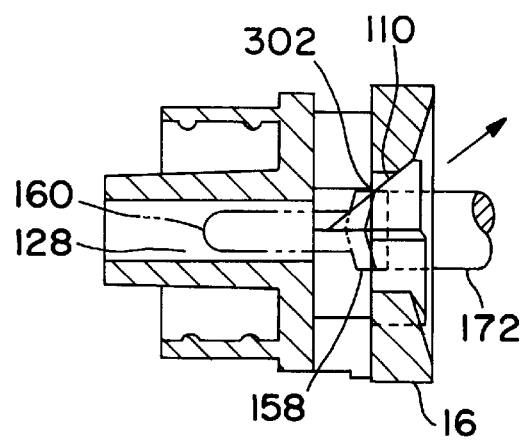
FIG. 21 is a cross-sectional view of the needle carrier of FIG. 20 taken along longitudinal section lines 21—21.
Figure 22:
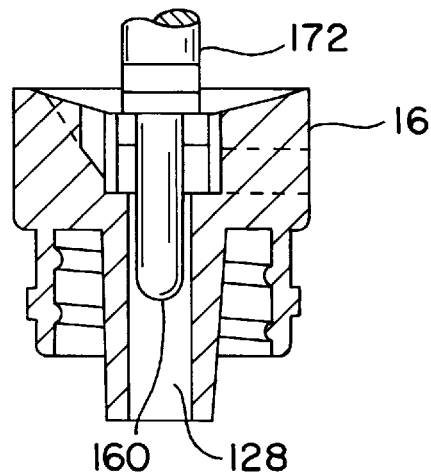
FIG. 22 is the view of FIG. 22A but with the plunger stinger before initial insertion into the pocket.
Figure 22A:
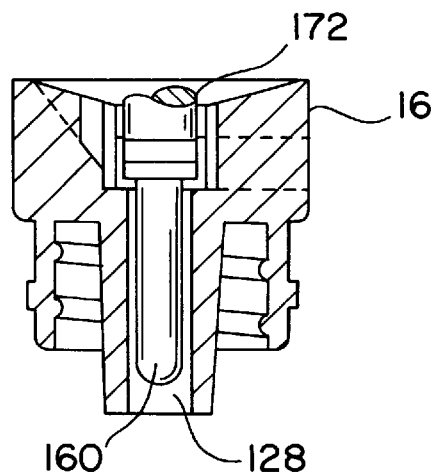
FIG. 22A is a ross-sectional view of the needle carrier of FIG. 23A taken along section lines 22—22 of FIG. 23A.
Figure 23A:
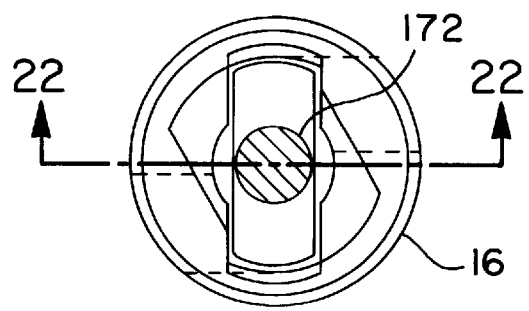
FIG. 23A is a distal view of the needle carrier of FIG. 8 which includes a partial cross-section of plunger stinger of FIG. 16 and FIG. 17 at initial insertion prior to clockwise rotation.
Figure 24:
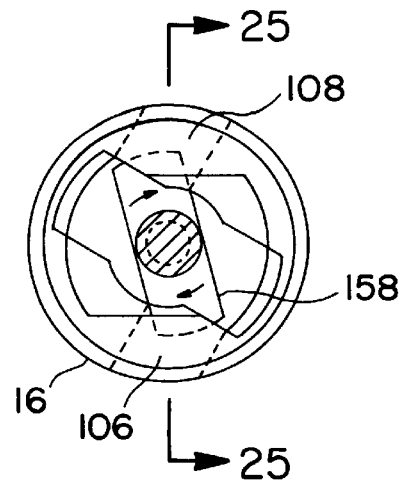
FIG. 24 is a distal view of the needle carrier of FIG. 8 which includes a partial cross-section of the plunger stinger of FIG. 16 and FIG. 17 after locking engagement of the stinger with the needle carrier.
Figure 25:
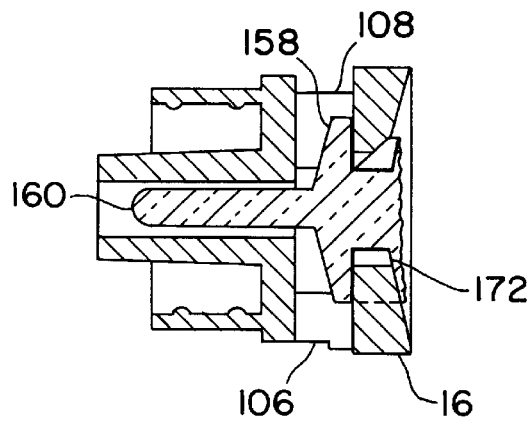
FIG. 25 is a longitudinal cross-sectional view of the preferred embodiment needle carrier of FIG. 24 taken along section lines 25—25.

At the proximal end of plunger 30 from detent 156, the stinger section is formed. It should be noted that the entire part shown in FIG. 16 is molded in one piece. Beginning at the end of detent 156 begins snap lock 164. Snap lock 164 is larger in diameter than the diameter of main body 150 of plunger 30. Further, the diameter of snap lock 164 is substantially the diameter of groove 48 (FIG. 11). Proximal of snap lock 164 is a short cylindrical portion 165 which terminates with plunger grooves 162 for the alternate embodiment and grooves 162A of the preferred embodiment at the proximal end of cylinder portion 165. Grooves 162, 162A are shaped to interlock with the interior piston rings 166, 166A, respectively, of the two embodiments of piston 32. Proximal to plunger grooves 162 or plunger grooves 162A, there is formed an extension or pedestal 172 extending from conical shaped base 174 and which terminates at stinger 158. The proximal end of stinger 158 includes a projection 160. Stinger 158 has a substantially rectangular shape that fits into stinger pocket 130 of needle carrier 16. Right hand rotation of stinger 158 into pockets 106 and 108 engage stinger with needle carrier 116 for rotation and removal of carrier 16 from mounting collar 14 of barrel 12, causing carrier 16 to be dismounted from needle mounting collar 14. See FIGS. 2, 22, 23, 23A, 24, 25, and 3 for the sequence of insertion of the singer assembly. Projection 160 fills the void space of luer opening 128 in order to reduce residual volume as shown by comparing the space taken by projection 160 in FIGS. 23, 23A. The stinger assembly further includes base or surface 174 which has a matching angle to the internal frusto conical surface 102 of carrier 16 in order to further reduce residual volume. Piston 32 shown in FIG. 19 and piston 32A shown in FIG. 19A fit over plunger grooves 162, 162A, respectively, such that plunger grooves 162, 162A, respectively engage with piston rings 166 or central way 166A, respectively. Pistons 32, 32A further include piston seals 168, 168A, respectively, which are in sliding and sealing engagement with the interior 78 of barrel 12. Pistons 32, 32A further include lips 170, 170A on both symmetrical ends of pistons 32, 32A, respectively. The purpose of lips 170, 170A is to provide a positive yet flexible stop for piston 32, 32A, respectively against carrier 16 prior to engagement and during engagement of the stinger 158 to carrier 16. FIG. 19A shows the preferred embodiment of piston 32A whereby piston 32A is approximately one-half the thickness of piston 32 shown in FIG. 19.

Plunger member 30 is provided with detent 156 in ribs 154 at a location such as to be substantially flush with the distal end of barrel 12 when the ring 164 is seated in grove 48 (FIG. 3). Lateral force may then be applied at the distal end of plunger 30 to break off the plunger 30 at the detent 156, leaving the remainder of the plunger 30 disposed inside barrel 12 with its distal end substantially flush with the distal end of barrel 12 in a locked position. FIG. 3 illustrates the plunger being broken off in this manner.

Figure 26:
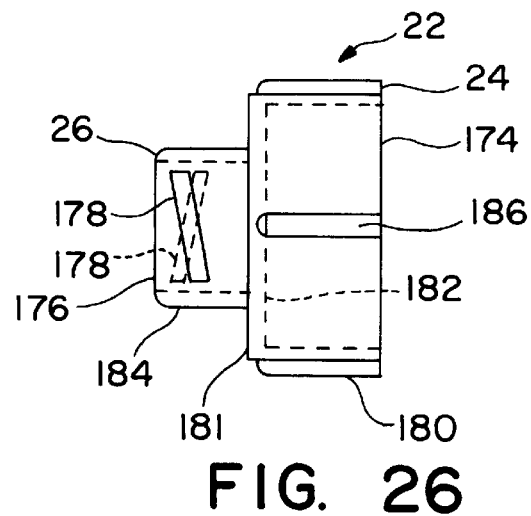
FIG. 26 is a side view of the preferred embodiment of the invertible barrel cap of the retractable syringe of FIG. 8.

As shown in FIG. 26, invertible cap 22 has two cylindrical portions 180, 184 which are concentric and co-axial, section 184 having a smaller diameter than section 180. Section 180 includes opening 174 formed in section 180, and co-axial to section 180, terminating at wall 182. Opening 174 is sized to form a frictional fit with outer surface 84 of barrel 12. The outer surface of large diameter portion 180 includes finger grips 186 to help rotate cap 22. Small diameter portion 184 abuts wall 182 and is stopped from fluid communication with large diameter portion 180 by wall 182. The opposite side of small diameter portion 184 from wall 182 includes opening 176 formed therein and co-axial with small diameter portion 184. Opening 176 terminates at wall 182. The difference in diameters between portion 184 and portion 180 causes the wall part 181 of wall 182 to be exterior of opening 176, forming a shoulder. On the exterior surface of small diameter cylinder 184 there are formed two threads 178 which are right hand and which are sized and angled to mate with surfaces 94 of threads 88 to form a connection upon right hand rotation of cap 22 after insertion of threads 178 into the open areas between threads 88. As set out above, the rotation causes threads 178 to cooperate with surfaces 94 to draw the cap 22 inward such that the proximal surface 91 of barrel 12 contacts and seals with surface 181 of cap 22. See FIGS. 3 and 26.

Figure 27:
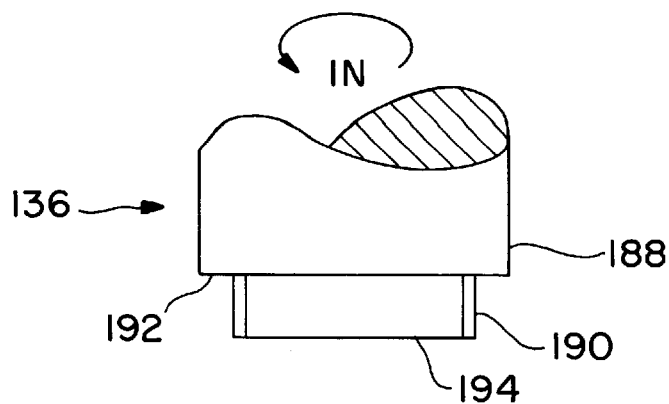
FIG. 27 is a side view of the preferred embodiment for the assembly tool used to assemble the needle carrier of FIG. 6 to the barrel mounting collar shown in FIG. 4.
Figure 28:
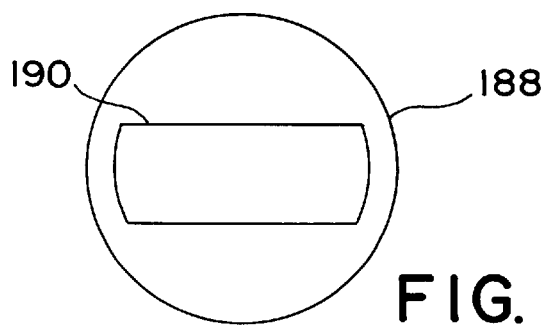
FIG. 28 is a proximal view of the assembly tool of FIG. 29.
Figure 29:
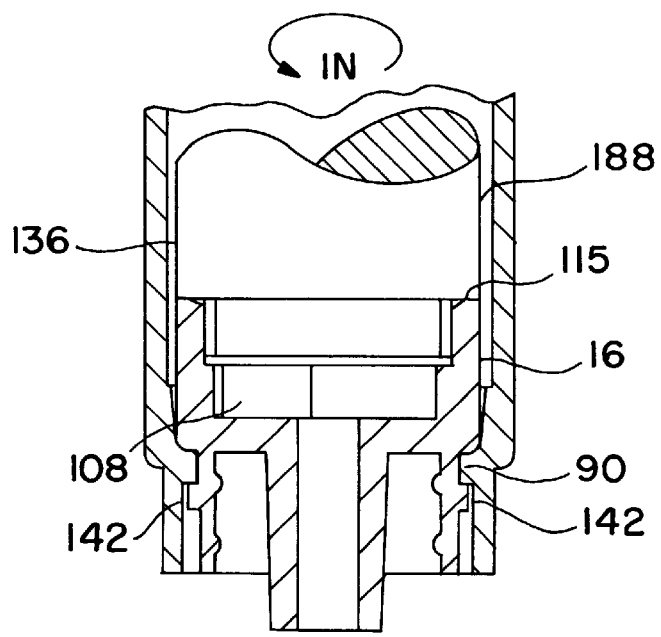
FIG. 29 is a partial cross-sectional assembly view of the assembly tool of FIG. 29 after assembly to the needle carrier of FIG. 6 in place in insertion showing arrow of preferred rotation for mounting.
Figure 30:
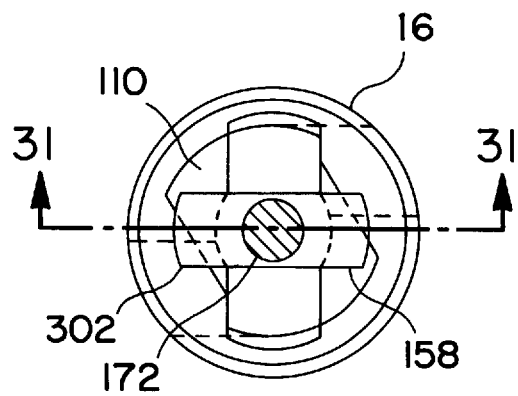
FIG. 30 is a distal end view of the preferred embodiment of the needle carrier which includes the plunger stinger shown on the conical surface at its maximum height during reverse or releasing counterclockwise rotation of the stinger from the carrier.
Figure 31:
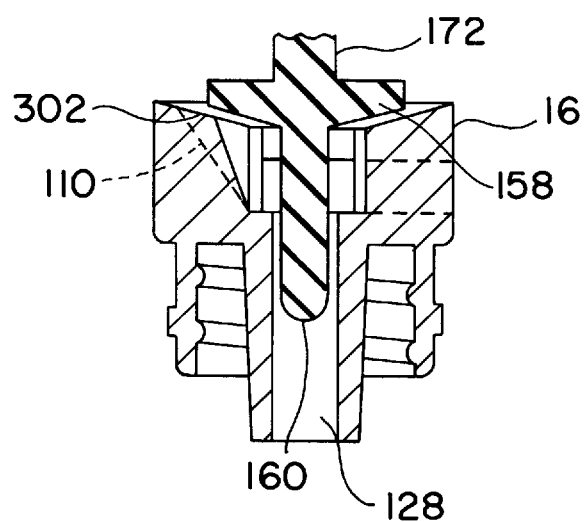
FIG. 31 is a cross-section view of the needle carrier of FIG. 30 taken along section lines 31—31.

Referring to FIGS. 27, 28 and 29, there is shown the assembly tool 136. The distal end of assembly tool 136 is a cylindrical body 188, sized to fit within the interior of barrel 12. At the proximal end of body 188 there is formed a key 190 which is also solid and is shaped to be inserted into key way 122, 124 and at such a length as to substantially bottom to key way bottom 126, 132. It should be noted that the key 190 length is such that it will not contact key bottom 126, 132, but instead the proximal facing surface 192 will be abut the distal surface 115 in order to pass force from tool 136 to needle carrier 16. Should the proximal surface 194 of key 190 contact the bottom 126, 132 of the key way, it could cause distortion of such bottom and a wedging out of the needle carrier 16 which could impair functionality.

In assembly, assembly tool 136 is first employed to mate with needle carrier 16 through key way 122, 124 and urges needle carrier 16 forward from the distal to the proximal end of the barrel and then rotates the needle carrier 16 onto lower internal quarter threads 90, forming a sealing interference fit with sealing surface 138 against surface 68. The tool is then removed by axial force towards the distal end and is replaced by plunger assembly 30, including piston 32 or piston 32A. In addition cap 22 opening 174 is frictionally applied to the proximal end of needle carrier 16, frictionally grasping wall 84 of barrel 12 to seal the proximal end of the barrel 12. The piston 32 or piston 32A seals the distal end of the barrel 12, thereby forming a sterile area.

The syringe 10 is now ready to be used, with piston 32 in sliding, sealing engagement with the interior wall of barrel 12. The syringe 10 is delivered to the person who will use it either in the assembled configuration shown in FIG. 1, or in a similar configuration but without a needle cartridge and needle mounted thereon. If the syringe 10 is delivered in the assembled configuration shown in FIG. 1, the operator may proceed to use it as is, or he or she may choose to remove the needle cartridge 18 and needle 20 supplied with a particular syringe 10 and replace it with another needle cartridge 18 and needle 20. Such a situation might arise, for example, if the operator wishes to use a needle of a different shape such as longer or shorter or of a different size, such as with a larger or smaller diameter and/or bore. If the operator wishes to replace needle cartridge 18 and needle 20, he or she grabs the needle cartridge firmly around the main body 216 and ribs 226 and rotates it in the appropriate direction, unscrewing the cartridge 18 from the needle carrier pocket 200. Preferably, during the removal and replacement procedure, a locking safety cover 50 remains on the needle cartridge 18 being removed and on the needle cartridge 18 being installed in its place. Locking safety covers 50 at this stage of the procedure will have their small ends around the needle cartridge 18 with needle 20 being safely received in tapered blind bores formed by covers 50 (FIG. 5). After removing the supplied needle cartridge, the operator then installs a desired needle in the cartridge 18 by grasping it firmly, preferably with its cover 50 in place, inserting its distal end into pocket 200 with member 206 entering bore 222, and rotating it in the appropriate direction to screw it securely into place.

If the syringe 10 were to be supplied with no needle cartridge 18 installed thereon, the operator simply has to install a desired needle cartridge 18 as set out above so that it is integral. In order to insure that a syringe 10 supplied without a needle cartridge is not contaminated prior to the time a needle cartridge is installed, it is preferred that a locking safety cover 22 be installed on surface 84 of mounting collar 14 when the syringe 10 is manufactured so as to protectively enclose the barrel 12. For this purpose, the larger end 180 of cover 22 is provided with actually extending blind bore 174 of a shape correlative to that of surface 84 and a diameter slightly smaller than the outside diameter of surface 84, so that when the cover 22 is forced over the surface 84, the cover 22 will stretch slightly and sealingly engage the surface 84. The fluid barrier 182 between the blind bore 174 and the blind bore 176 of cover 22 prevents fluid communication between the bores.

Subsequently when the needle is ready to be used with the syringe, cover 50 would be removed and the syringe would be used either to take samples or to give injections or other biomedical needs. At this point, piston 36 is free to be moved by plunger 30 to a position just short of latching engagement between stinger 158 and needle carrier 16. As discussed above, the operator may then remove cover 50 from needle cartridge 18 and needle 20, and proceed to draw a liquid or fluid substances from a container through needle 20 into barrel 12 and inject it into a subject or insert the needle 20 into a subject with barrel 12 empty and withdraw blood or other fluids from the subject for disposing into a container for testing or the like.

Once the needle 20 has completed its usage, it is ready to be retracted. Retraction occurs by moving the plunger 30 and piston 32, 32A as far proximal forward as they will travel. Needle carrier stinger 158 includes extension or projection 160 and base 174 which causes displacement of fluid within the opening 102 and luer opening 128 to reduce the internal volume of the needle carrier or to reduce the residual volume within the syringe after injection. Also, piston 32 includes symmetrical lips 170 also further reduce residual volume within the syringe after injection. Thus, after an injection and before rotation, the residual volume of any excess fluid remaining is substantially lower, thereby substantially reducing any "squirt" of fluids or substantially reducing squirt of fluids that might be entrained in residual spaces prior to activation of the rotation mechanism.

For removing the needle into the body 12, stinger 158 is inserted into carrier 16 and in particular into pocket 131. Stinger 158 is inserted into carrier 16 by having plunger member 30 pushed firmly in a proximal direction until stinger 158 is forced into pocket 131 in needle carrier 16. It is then rotated into pockets 106, 108, the rotation into pockets 106, 108, thereby engaging the restriction boundary surfaces of passages 106, 108. Further clockwise rotation causes carrier 16 to rotate with plunger 30 and causes it to disengage from threads 90. Axial force applied towards the distal end after disengagement of threads 90 will permit the needle 20 to be withdrawn into the interior of barrel 12. Further drawing of the plunger 30 in a distal direction will cause ring 164 to be snapped into groove 48. Whether or not groove 48 is used, the distal portion of the plunger member 30 is broken off at detent 156, leaving the broken end of the plunger 30 substantially flush with the end of the barrel 12, and if groove 48 is used, the remainder of the plunger 30 securely latched within the barrel 12. The needle cartridge 18 and needle 20 are thus securely retained and immobilized in protective isolation within the barrel 12, as shown in FIG. 3. The protective cover 22 may then be installed in the collar 14 as shown in FIG. 3 in order to prevent excess fluids or residue remaining in the syringe 10 from leaking out of the syringe. The used syringe may then be safely discarded without further danger of a needle stick injury.

In the event that an attempt is made to reinsert the assembly at the proximal end of the plunger 30, which is locked in the interior of the barrel 12, so that the needle carrier 16 is again engaged with collar 14, first the plunger 30 would need to be forced over snap shoulder or proximal constriction 52. If this were accomplished and stinger 158 were reinserted into stinger opening 130 to rest at the end of pocket 131, the leading edge 302 of stinger 158 will contact and slide against the upper surface 110 of carrier 16, until it reaches the highest conical ledge and then would fall back in the slot, preventing reengagement of stinger 158 by reverse rotation with needle carrier 16 by sliding along surface 110. See FIGS. 30, 31, 20, 21 and 22 for the sequence of preventing reattachment of carrier 16 with collar 14. Thus, no force may be applied by the stinger 158 to the carrier 16 to cause reengagement of the carrier 16 with the mounting collar 14. Only the tool 136 can do this.

While preferred and alternate embodiments of the invention have been shown and described, many modifications thereof may be made by those skilled in the art without parting from the spirit of this invention. Therefore, the scope of the invention should be determined in accordance with the following claims.

What is claimed is:

1. A retractable syringe for use with a hypodermic needle cartridge, comprising:
    a barrel having a proximal end and a distal end, said proximal end of said barrel including a mounting collar with a bore having a wall;
    a piston plunger telescopingly received within said distal end of said barrel, said plunger including a snap lock coaxial with said plunger;
    a needle carrier located at said proximal end of said barrel;
    a groove formed in said wall and having a distal constriction and a proximal constriction, said groove being located near said distal end of said barrel, the width of said groove being at least equal to the width of said snap lock;
    said distal constriction and said proximal constriction each having an interior diameter less than the diameter of said groove and each having a proximal side and a distal side;
    said distal constriction interior diameter being smaller than said proximal constriction interior diameter;
    a first angle formed between said wall and said distal constriction distal side;
    a second angle formed between said groove and said distal constriction proximal side;
    said first angle being greater than said second angle;
    a third angle formed between said groove and said proximal constriction distal side;
    a fourth angle formed between said wall and said proximal constriction proximal sides;
    said fourth angle being greater than said third angle.

2. The syringe of claim 1, wherein said first angle is approximately the same as said fourth angle.

3. The syringe of claim 2, wherein said second angle is approximately the same as said third angle.

4. The syringe of claim 1, wherein said second angle is approximately the same as said third angle.

5. The syringe of claim 1, wherein the interior diameter of said groove is approximately equally to the interior diameter of said wall.

6. The syringe of claim 1, wherein the cross section of said distal constriction is a truncated triangular shape.

7. The syringe of claim 6, wherein the base of said triangle has an interior diameter approximately equal to the interior of diameter of said wall.

8. The syringe of claim 1, wherein the cross section of said proximal constriction is a truncated triangular shape.

9. The syringe of claim 8, wherein the base of said triangle has an interior diameter approximately equal to the interior of diameter of said wall.

10. The syringe of claim 1, wherein the cross section of said distal constriction is a trapezoid shape in cross shape.

11. The syringe of claim 10, wherein the base of said trapezoid has an interior diameter approximately equal to the interior of diameter of said wall.

12. The syringe of claim 1, wherein the cross section of said proximal constriction is a trapezoid shape in cross section.

13. The syringe of claim 12, wherein the base of said trapezoid has an interior diameter approximately equal to the interior of diameter of said wall.

14. The syringe of claim 1, wherein said distal constriction has a inner cylindrical shaped surface having an axial extension, said axial extension having an axial length equal to at least twice the difference between the radius of said wall and the radius of said cylindrical shaped surface.

15. The syringe of claim 1, wherein the depth of said proximal constriction is approximately one-half of the depth of said distal constriction.

* * * * *